(12) United States Patent
Moeckel et al.

(10) Patent No.: US 7,173,105 B2
(45) Date of Patent: Feb. 6, 2007

(54) NUCLEOTIDE SEQUENCES CODING FOR THE LUXR GENE

(75) Inventors: Bettina Moeckel, Duesselforf (DE); Caroline Kreutzer, Melle (DE); Brigitte Bathe, Salzkotten (DE)

(73) Assignee: Degussa AG, Duesseldorf (DE)

( * ) Notice: Subject to any disclaimer, the term of this patent is extended or adjusted under 35 U.S.C. 154(b) by 211 days.

(21) Appl. No.: 11/020,188

(22) Filed: Dec. 27, 2004

(65) Prior Publication Data

US 2006/0134761 A1    Jun. 22, 2006

Related U.S. Application Data

(62) Division of application No. 09/903,771, filed on Jul. 13, 2001, now Pat. No. 6,875,586.

(30) Foreign Application Priority Data

Aug. 10, 2000   (DE)   ................. 100 39 043

(51) Int. Cl.
*C12P 13/04* (2006.01)
*C12P 13/08* (2006.01)
*C12N 15/01* (2006.01)
*C12N 15/31* (2006.01)
*C12N 15/77* (2006.01)

(52) U.S. Cl. ................. 530/106; 435/115; 435/252.3; 435/320.1; 435/463; 435/471; 536/23.1

(58) Field of Classification Search ............ None
See application file for complete search history.

(56) References Cited

U.S. PATENT DOCUMENTS 6,815,196 B2 * 11/2004 Bathe et al. ............ 435/252.33
6,875,586 B2 *  4/2005 Moeckel et al. .......... 435/69.1
2002/0197605 A1 * 12/2002 Nakagawa et al. ............ 435/6
2005/0153402 A1 *  7/2005 Pompejus et al. .......... 435/106
2005/0277115 A1 * 12/2005 Pompejus et al. ............ 435/6

FOREIGN PATENT DOCUMENTS

| EP | 1108790 A2 | 6/2001 |
| WO | WO 01/00802 | 1/2001 |
| WO | WO 01/00842 | 1/2001 |
| WO | WO 01/00845 | 1/2001 |
| WO | WO 01/00847 | 1/2001 |

OTHER PUBLICATIONS

Choi, S. H., and Greenberg, E. P., 1992, "Genetic dissection of DNA binding and luminescence gene activation by the *Vibrio fischeri* LuxR protein", Journal of Bacteriology, vol. 174, No. 2, pp. 4064-4069.*

Sitnikov, D. M., et al., 1996, "Autoinducer-independent mutants of the LuxR transcriptioal activator exhibit differential effects on the two lux promoters of *Vibrio fischeri*", Molecular and General Genetics, vol. 252, No. 5, pp. 622-625.*

S. Nakagawa, et al., Database EMBL Online, AN AX123320, XP-002189178, pp. 1-3, "Novel Polynucleotides Derived From *Coryneform* Bacteria", May 10, 2001.

(Continued)

*Primary Examiner*—Nashaat T. Nashed
*Assistant Examiner*—William W. Moore
(74) *Attorney, Agent, or Firm*—Oblon, Spivak, McClelland, Maier & Neustadt, P.C.

(57) ABSTRACT

The present invention relates to polynucleotides corresponding to the luxR gene and which encode a LuxR transcriptional activator, methods of producing L-amino acids, and methods of screening for polynucleotides which encode proteins having LuxR transcriptional activation activity.

9 Claims, 1 Drawing Sheet

OTHER PUBLICATIONS

Database EMBL "Online", XP-002189179, pp. 1-3, WO 01/00842, Jan. 4, 2001.

M.P. Schmitt, Journal of Bacteriology, vol. 181, No. 17, pp. 5330-5340, "Identification of a Two-Component Signal Transduction System From *Corynebacterium diphtheriae* That Activates Gene Expression in Response to the Presence of Heme and Hemoglobin", Sep. 1999; and Database EMBL "Online", AN AF161327, XP-002189180, 4 Pages, "Response Regulator of Two Component Signal Transduction System", Jul. 30, 1999.

B. J. Eikmanns, et al., Antonie Van Leeuwenhoek, XP-000918559, vol. 64, No. 2, pp. 145-163, "Molecular Aspects of Lysine, Threonine, and Isoleucine Biosynthesis in *Corynebacterium glutamicum*", 1993.

M. Vrljic, et al., Molecular Microbiology, XP-000675494, vol. 22, No. 5, pp. 815-826, "A New Type of Transporter with a New Type of Cellular Function: L-Lysine Export From *Corynebacterium glutamicum*", Dec. 1, 1996.

\* cited by examiner

Figure 1: Plasmid map of pCR2.1luxRint
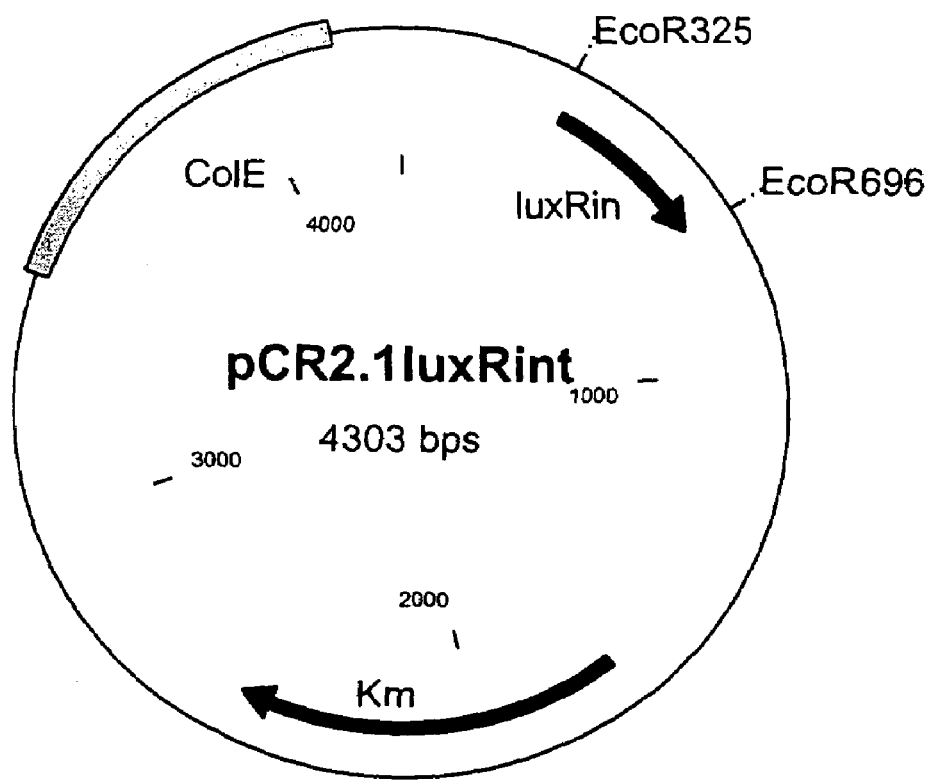

NUCLEOTIDE SEQUENCES CODING FOR THE LUXR GENE

CROSS-REFERENCE TO RELATED APPLICATIONS

The present application is a divisional application of U.S. Ser. No. 09/903,771 filed on Jul. 13, 2001, now U.S. Pat. No. 6,875,586, and claims priority to German Application No. DE 10039043.9 filed Aug. 10, 2000, the entire contents of which are incorporated herein by reference.

BACKGROUND OF THE INVENTION

1. Field of the Invention

The invention provides nucleotide sequences from Coryneform bacteria which code for the luxR gene and a process for the fermentative preparation of amino acids, in particular L-lysine by attenuation of the luxR gene. The luxR gene codes for the LuxR protein, which is a transcription activator.

2. Discussion of the Background

L-amino acids, particularly L-lysine, are used in human medicine and in the pharmaceuticals industry, in the foodstuffs industry and, most particularly, in the feeding of animals.

It is known that amino acids are produced by fermentation of strains of Coryneform bacteria, in particular Corynebacterium glutamicum. Because of their great importance, attempts are continuously being made to improve the production processes. Improvements to the processes may concern measures relating to the fermentation, such as, for example, stirring and oxygen supply, or the composition of the nutrient media, such as, the sugar concentration during the fermentation, or working up to the product form by, for example, ion-exchange chromatography, or the intrinsic performance properties of the microorganism itself.

In order to improve the performance properties of such microorganisms, methods of mutagenesis, selection and mutant selection are employed. Such methods yield strains which are resistant to antimetabolites or are auxotrophic for metabolites that are important in terms of regulation, and which produce amino acids.

For a number of years, methods of recombinant DNA technology have also been used for improving the strain of L-amino acid-producing strains of Corynebacterium. However, there remains a critical need for improved methods of producing L-amino acids and thus for the provision of strains of bacteria producing higher amounts of L-amino acids. On a commercial or industrial scale even small improvements in the yield of L-amino acids, or the efficiency of their production, are economically significant. Prior to the present invention, it was not recognized that attenuation of luxR gene encoding the a LuxR transcriptional activator protein would improve L-amino acid yields.

SUMMARY OF THE INVENTION

The inventors have set themselves the object of providing novel measures for the improved production of amino acids, in particular L-lysine, by fermentation.

One object of the present invention, is providing a new process adjuvant for improving the fermentative production of L-amino acids, particularly L-lysine and L-glutamate. Such process adjuvants include enhanced bacteria, preferably enhanced Coryneform bacteria which express attenuated amounts of the LuxR transcriptional activator which is encoded by the luxR gene.

Thus, another object of the present invention is providing such an bacterium, which expresses an attenuated amount of LuxR transcriptional activator or gene products of the luxR gene.

Another object of the present invention is providing a bacterium, preferably a Coryneform bacterium, which expresses a polypeptide that has an attenuated LuxR transcriptional activation activity.

Another object of the invention is to provide a nucleotide sequence encoding a polypeptide which has LuxR transcriptional activator sequence. One embodiment of such a sequence is the nucleotide sequence of SEQ ID NO: 1.

A further object of the invention is a method of making LuxR transcriptional activator or an isolated polypeptide having a LuxR transcriptional activator activity, as well as use of such isolated polypeptides in the production of amino acids. One embodiment of such a polypeptide is the polypeptide having the amino acid sequence of SEQ ID NO: 2.

Other objects of the invention include methods of detecting nucleic acid sequences homologous to SEQ ID NO: 1, particularly nucleic acid sequences encoding polypeptides that have LuxR transcriptional activator activity, and methods of making nucleic acids encoding such polypeptides.

The above objects highlight certain aspects of the invention. Additional objects, aspects and embodiments of the invention are found in the following detailed description of the invention.

BRIEF DESCRIPTION OF THE DRAWING

FIG. 1: Map of plasmid pCR2.1luxRint

DETAILED DESCRIPTION OF THE INVENTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory, New York (1982) and Sambrook et al., Molecular Cloning: A Laboratory Manual, Cold Spring Harbor Laboratory, New York (1989) and the various references cited therein.

The invention provides an isolated polynucleotide from Coryneform bacteria, containing a polynucleotide sequence coding for the luxR gene, selected from the group a) polynucleotide that is at least 70% identical with a polynucleotide that codes for a polypeptide containing the amino acid sequence of SEQ ID No. 2, b) polynucleotide that codes for a polypeptide containing an amino acid sequence that is at least 70% identical with the amino acid sequence of SEQ ID No. 2, c) polynucleotide that is complementary to the polynucleotide of a) or b), and I d) polynucleotide containing at least 15 consecutive nucleotides of the polynucleotide sequence of a), b) or c), the polypeptide preferably exhibiting the activity of the transcription activator LuxR.

The invention also provides the above-mentioned polynucleotide, it preferably being a replicatable DNA containing:

(i) the nucleotide sequence shown in SEQ ID No. 1, or (ii) at least one sequence that corresponds to sequence (i) within the region of the degeneracy of the genetic code, or (iii) at least one sequence that hybridizes with the sequences that are complementary to sequence (i) or (ii), and optionally (iv) sense mutations in (i) that are neutral in terms of function.

The invention also provides:

a replicatable DNA containing the nucleotide sequence as shown in SEQ ID No. 1;

a polynucleotide that codes for a polypeptide containing the amino acid sequence as shown in SEQ ID No. 2;

a vector containing the polynucleotide accpording to the invention, point d, particularly pCR2.1luxRint, deposited in *Escherichia coli* DSM 13619 at the DSMZ, Braunschweig (Germany);

and *Coryneform* bacteria that contain in the luxR gene an insertion or deletion, particularly using the vector pCR2.1luxRint.

The invention also provides polynucleotides consisting substantially of a polynucleotide sequence, which are obtainable by screening, by means of hybridization, a corresponding gene library that contains the complete gene having the polynucleotide sequence according to SEQ ID No. 1, using a probe containing the sequence of the mentioned polynucleotide according to SEQ ID No. 1 or a fragment thereof, and isolating the mentioned DNA sequence.

Polynucleotide sequences according to the invention are suitable as hybridization probes for RNA, cDNA and DNA, in order to isolate in their complete length nucleic acids or polynucleotides or genes that code for the LuxR protein, or in order to isolate nucleic acids or polynucleotides or genes that have a high degree of similarity with the sequence of the luxR gene.

Polynucleotide sequences according to the invention are also suitable as primers, with the aid of which it is possible, by means of the polymerase chain reaction (PCR), to produce DNA of genes that code for the LuxR protein.

Such oligonucleotides acting as probes or primers contain at least 30, preferably at least 20, more preferably at least 15, consecutive nucleotides. Also suitable are oligonucleotides having a length of at least 40 or 50 nucleotides.

"Isolated" means removed from its natural environment.

"Polynucleotide" generally refers to polyribonucleotides and polydeoxyribonucleotides, it being possible for the RNA or DNA to be unmodified or modified.

"Polypeptides" are to be understood as being peptides or proteins that contain two or more amino acids bonded via peptide bonds.

The polypeptides according to the invention include a polypeptide according to SEQ ID No. 2, particularly those having the biological activity of the LuxR protein, and also those that are at least 700, preferably at least 80% and in particular at least from 90% to 95% identical with the polypeptide according to SEQ ID No. 2, and exhibit the mentioned activity.

The invention also provides a process for the production of amino acids, particularly L-lysine, by fermentation using *Coryneform* bacteria which, in particular, already produce amino acids and in which the nucleotide sequences coding for the luxR gene are attenuated, in particular excluded or expressed at a low level.

The term "attenuation" in this connection describes the diminution or exclusion of the intracellular activity of one or more enzymes (proteins) in a microorganism that are coded for by the corresponding DNA, by, for example, using a weak promoter or using a gene or allele that codes for a corresponding enzyme having low activity, or by inactivating the corresponding gene or enzyme (protein), and optionally by combining those measures.

The microorganisms provided by the present invention are able to produce amino acids, in particular L-lysine, from glucose, saccharose, lactose, fructose, maltose, molasses, starch, cellulose or from glycerol and ethanol. They may be representatives of *Coryneform* bacteria, particularly of the genus *Corynebacterium*. In the case of the genus *Corynebacterium*, special mention may be made of the species *Corynebacterium glutamicum*, which is known to those skilled in the art for its ability to produce L-amino acids.

Suitable strains of the genus *Corynebacterium*, particularly of the species *Corynebacterium glutamicum* (*C. glutamicum*), are, in particular, the known wild-type strains

*Corynebacterium glutamicum* ATCC 13032
*Corynebacterium acetoglutamicum* ATCC 15806
*Corynebacterium acetoacidophilum* ATCC13870
*Corynebacterium melassecola* ATCC 17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020 or L-amino acid-producing mutants or strains prepared therefrom, such as, the L-lysine-producing strains

*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464
*Corynebacterium glutamicum* DM58-1
*Corynebacterium glutamicum* DG52-5
*Corynebacterium glutamicum* DSM 5714 and
*Corynebacterium glutamicum* DSM 12866.

Preferably, a bacterial strain with attenuated expression of a luxR gene that encodes a polypeptide with LuxR transcriptional activation activity will improve amino acid yield at least 1%.

The inventors have succeeded in isolating the new luxR gene of *C. glutamicum* that codes for the LuxR protein, which gene is a transcription activator.

In order to isolate the luxR gene or also other genes of *C. glutamicum*, a gene library of that microorganism in *Escherichia coli* (*E. coli*) is first prepared. The preparation of gene libraries is written down in generally known textbooks and handbooks. For example, the textbook of Winnacker: Gene and Klone, Eine Einfiihrung in die Gentechnologie (Verlag Chemie, Weinheim, Germany, 1990) or the handbook of Sambrook et al.: Molecular Cloning, A Laboratory Manual (Cold Spring Harbor Laboratory Press, 1989). A very well known gene library is that of the *E. coli* K-12 strain W3110, which has been prepared by Kohara et al. (Cell 50, 495–508 (1987)) in vectors. Bathe et al. (Molecular and General Genetics, 252:255–265, 1996) describe a gene library of *C. glutamicum* >ATCC13032, which has been prepared with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575). Bormann et al. (Molecular Microbiology 6(3), 317–326 (1992)) in turn describe a gene library of *C. glutamicum* ATCC13032 using the cosmid pHC79 (Hohn and Collins, 1980, Gene 11, 291–298).

For the preparation of a gene library of *C. glutamicum* in *E. coli* it is also possible to use plasmids such as pBR322 (Bolivar, 1979, Life Sciences, 25, 807–818) or pUC9 (Vieira et al., 1982, Gene, 19:259–268). Suitable hosts are particularly those *E. coli* strains that are restriction and recombination-defective, such as, the strain DH5α, (Jeffrey H. Miller: "A Short Course in Bacterial Genetics, A Laboratory Manual and Handbook for *Escherichia coli* and Related Bacteria", Cold Spring Harbour [sic] Laboratory Press, 1992).

The long DNA fragments cloned with the aid of cosmids or other λ-vectors can then in turn be subcloned into customary vectors suitable for DNA sequencing.

Methods of DNA sequencing are described inter alia in Sanger et al. (Proceedings of the National Academy of Sciences of the United States of America USA, 74:5463–5467, 1977).

The resulting DNA sequences can then be studied using known algorithms or sequence-analysis programs, such as, that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)).

In that manner, the novel DNA sequence of *C. glutamicum* coding for the luxR gene has been obtained, which sequence, as SEQ ID No. 1, forms part of the present invention. Furthermore, the amino acid sequence of the corresponding protein has been derived from the present DNA sequence using the methods described above. The resulting amino acid sequence of the luxR gene product is shown in SEQ ID No. 2.

Coding DNA sequences that result from SEQ ID No. 1 by the degeneracy of the genetic code also form part of the invention. Likewise, DNA sequences that hybridize with SEQ ID No. 1 or parts of SEQ ID No. 1 form part of the invention. Furthermore, to those skilled in the art, conservative amino acid substitutions, such as, for example, the substitution of glycine with alanine or of aspartic acid with glutamic acid, in proteins are known as sense mutations, which do not lead to any fundamental change in the activity of the protein, that is to say are neutral in terms of function. It is also known that changes at the N- and/or C-terminus of a protein do not substantially impair its function or may even stabilise it. The person skilled in the art will find relevant information inter alia in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences that result in a corresponding manner from SEQ ID No. 2 likewise form part of the invention.

Finally, DNA sequences that are produced by the polymerase chain reaction (PCR) using primers that result from SEQ ID No. 1 form part of the invention. Such oligonucleotides typically have a length of at least 15 nucleotides.

The person skilled in the art will find instructions on the identification of DNA sequences by means of hybridization inter alia in the handbook "The DIG System Users Guide for Filter Hybridization" from Boehringer Mannheim GmbH (Mannheim, Germany, 1993) and in Liebl et al. (International Journal of Systematic Bacteriology 41: 255–260 (1991)). The person skilled in the art will find instructions on the amplification of DNA sequences with the aid of the polymerase chain reaction (PCR) inter alia in the handbook of Gait: Oligonukleotide [sic] Synthesis: A Practical Approach (IRL Press, Oxford, UK, 1984) and in Newton and Graham: PCR (Spektrum Akademischer Verlag, Heidelberg, Germany, 1994).

During work on the present invention it has been found that *Coryneform* bacteria produce amino acids, in particular L-lysine, in an improved manner after attenuation of the luxR gene.

In order to achieve attenuation, either the expression of the luxR gene or the catalytic properties of the enzyme protein can be diminished or excluded. The two measures may optionally be combined.

A diminution of gene expression can be effected by carrying out the culturing in a suitable manner or by genetic alteration (mutation) of the signal structures of gene expression. Signal structures of gene expression are, for example, repressor genes, activator genes, operators, promoters, attenuators, ribosome-binding sites, the start codon and terminators. The person skilled in the art will find information thereon, for example, in patent application WO 96/15246, in Boyd and Murphy (Journal of Bacteriology 170: 5949 (1988)), in Voskuil and Chambliss (Nucleic Acids Research 26: 3548 (1998), in Jensen and Hammer (Biotechnology and Bioengineering 58: 191 (1998)), in Patek et al. (Microbiology 142: 1297 (1996)), Vasicova et al. (Journal of Bacteriology 181: 6188 (1999)) and in known textbooks of genetics and molecular biology, such as, for example, the textbook of Knippers ("Molekulare Genetik", 6th edition, Georg Thieme Verlag, Stuttgart, Germany, 1995) or that of Winnacker ("Gene and Klone", VCH Verlagsgesellschaft, Weinheim, Germany, 1990).

Mutations that lead to a change in or diminution of the catalytic properties of enzyme proteins are known from the prior art; examples which may be mentioned are the works of Qiu and Goodman (Journal of Biological Chemistry 272: 8611–8617 (1997)), Sugimoto et al. (Bioscience Biotechnology and Biochemistry 61: 1760–1762 (1997)) and Mockel ("Die Threonindehydratase aus *Corynebacterium glutamicum*: Aufhebung der allosterischen Regulation and Struktur des Enzyms", Reports from the Julich Research Centre, Jut-2906, ISSN09442952, Julich, Germany 1994).

Summaries are to be found in known textbooks of genetics and molecular biology, such as, that of Hagemann ("Allgemeine Genetik", Gustav Fischer Verlag, Stuttgart, 1986).

There come into consideration as mutations transitions, transversions, insertions and deletions. In dependence on the effect of the amino acid substitution on the enzyme activity, missense mutations or nonsense mutations are referred to. Insertions or deletions of at least one base pair (bp) in a gene lead to frame shift mutations, as a result of which incorrect amino acids are incorporated or the translation breaks off prematurely. Deletions of several codons typically result in a complete loss of enzyme activity. Instructions for the production of such mutations are part of the prior art and are to be found in known textbooks of genetics and molecular biology, such as, for example, the textbook of Knippers ("Molekulare Genetik", 6th edition, Georg Thieme Verlag, Stuttgart, Germany, 1995), that of Winnacker ("Gene and Klone", VCH I Verlagsgesellschaft, Weinheim, Germany, 1990) or that of Hagemann ("Allgemeine Genetik", Gustav Fischer Verlag, Stuttgart, 1986).

A common method of mutating genes of *C. glutamicum* is the method of gene disruption and of gene replacement described by Schwarzer and Pühler (Bio/Technology 9, 84–87 (1991)).

In the method of gene disruption, a central portion of the coding region of the gene in question is cloned into a plasmid vector which is able to replicate in a host (typically *E. coli*), but not in *C. glutamicum*. Suitable vectors are, for example, pSUP301 (Simon et al., Bio/Technology 1, 784–791 (1983)), pK18mob or pK19mob (Schafer et al., Gene 145, 69–73 (1994)), pK18mobsacB or pK19mobsacB (lager et al., Journal of Bacteriology 174: 5462–5465 (1992)), pGEM-T (Promega corporation, Madison, Wis., USA), pCR2.1-TOPO (Shuman (1994). Journal of Biological Chemistry 269:32678–32684; U.S. Pat. No. 5,487,993), pCR®Blunt (Invitrogen, Groningen, Netherlands; Bernard et al., Journal of Molecular Biology, 234: 534–541 (1993)) or pEM1 (Schrumpfet al., 1991, Journal of Bacteriology 173:45104516). The plasmid vector containing the central portion of the coding region of the gene is then transferred to the desired strain of *C. glutamicum* by conjugation or transformation. The method of conjugation is described, for example, in Schafer et al (Applied and Environmental Microbiology 60, 756–759 (1994)). Methods of transformation are described, for example, in Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a cross-over occurrence, the coding region of the gene in question is disrupted by the vector sequence, and two incomplete alleles lacking the 3'- and the 5'-end, respectively, are obtained. That method has been used, for example, by Fitzpatrick et al. (Applied Microbiology and Biotechnology 42, 575–580 (1994)) to exclude the recA gene of *C. glutamicum*.

FIG. 1 shows by way of example the plasmid vector pCR2.1luxRint, by means of which the luxR gene can be disrupted or excluded.

In the gene replacement method, a mutation, such as, for example, a deletion, insertion or base substitution, is produced in vitro in the gene in question. The allele that is produced is in turn cloned into a vector that is not replicative for *C. glutamicum*, and the latter is then transferred to the desired host of *C. glutamicum* by transformation or conjugation. After homologous recombination by means of a first cross-over occurrence effecting integration and by means of a suitable second cross-over occurrence effecting an excision in the target gene or in the target sequence, incorporation of the mutation or of the allele is achieved. That method has been used, for example, by Peters-Wendisch et al. (Microbiology 144, 915–927 (1998)) to exclude the pyc gene of *C. glutamicum* by means of a deletion.

A deletion, insertion or a base substitution may thus be incorporated into the luxR gene.

In addition, it may be advantageous for the production of L-amino acids, particularly L-lysine, in addition to attenuating the luxR gene, to amplify, in particular to overexpress, one or more enzymes of the biosynthesis pathway in question, of glycolysis, of the anaplerotic pathway, of the pentose phosphate cycle or of amino acid export.

Accordingly, for example for the production of L-lysine, one or more genes selected from the group the gene dapA coding for dihydrodipicolinate synthase (EP-B 0 197 335), the gene eno coding for enolase (DE: 19947791.4), the gene zwf coding for the zwf gene product (JP-A-09224661), the gene pyc coding for pyruvate carboxylase (Peters-Wendisch et al. (Microbiology 144, 915–927 (1998)), the gene lysE coding for lysine export (DE-A-195 48 222)

may at the same time be enhanced, in particular overexpressed.

In addition, it may be advantageous for the production of amino acids, particularly L-lysine, in addition to attenuation of the luxR gene, at the same time to attenuate one or more genes selected from the group the gene pck coding for phosphoenol pyruvate carboxykinase (DE 199 50 409.1, DSM 13047), the gene pgi coding for glucose-6-phosphate isomerase (U.S. Ser. No. 09/396,478, DSM 12969), the gene poxB coding for pyruvate oxidase (DE:1995 1975.7, DSM 13114).

It may also be advantageous for the production of amino acids, particularly L-lysine, in addition to attenuating the luxR gene, to exclude undesired secondary reactions (Nakayama: "Breeding of Amino Acid Producing Microorganisms", in: Overproduction of Microbial Products, Krumphanzl, Sikyta, Vanek (eds.), Academic Press, London, UK, 1982).

The microorganisms produced according to the invention also form part of the invention and can be cultivated, for the purposes of the production of L-amino acids, in particular L-lysine, continuously or discontinuously in the batch, fed batch or repeated fed batch process. A summary of known cultivation methods are [sic] described in the textbook of Chmiel (Bioprozesstechnik 1. Einfiihrung in die Bioverfahrenstechnik (Gustav Fischer Verlag, Stuttgart, 1991)) or in the textbook of Storhas (Bioreaktoren and periphere Einrichtungen (Vieweg Verlag, Braunschweig/Wiesbaden, 1994)).

The culture medium to be used must meet the requirements of the strains in question in a suitable manner. Descriptions of culture media for various microorganisms are to be found in the handbook "Manual of Methods for General Bacteriology" of the American Society for Bacteriology (Washington D.C., USA, 1981). There may be used as the carbon source sugars and carbohydrates, such as, for example, glucose, saccharose, lactose, fructose, maltose, molasses, starch and cellulose, oils and fats, such as, for example, soybean oil, sunflower oil, groundnut oil and coconut oil, fatty acids, such as, for example, palmitic acid, stearic acid and linoleic acid, alcohols, such as, for example, glycerol and ethanol, and organic acids, such as, for example, acetic acid. Those substances may be used individually or in the form of a mixture.

There may be used as the nitrogen source organic nitrogen containing compounds, such as peptones, yeast extract, meat extract, malt extract, corn steep liquor, soybean flour and urea, or inorganic compounds, such as ammonium sulfate, ammonium chloride, ammonium phosphate, ammonium carbonate and ammonium nitrate. The nitrogen sources may be used individually or in the form of a mixture.

There may be used as the phosphorus source phosphoric acid, potassium dihydrogen phosphate or dipotassium hydrogen phosphate or the corresponding sodium-containing salts. The culture medium must also contain salts of metals, such as, for example, magnesium sulfate or iron sulfate, which are necessary for growth. Finally, essential growth substances, such as amino acids and vitamins, may be used in addition to the above-mentioned substances. Suitable precursors may also be added to the culture medium. The mentioned substances may be added to the culture in the form of a single batch, or they may be fed in in a suitable manner during the cultivation.

In order to control the pH value of the culture, basic compounds, such as sodium hydroxide, potassium hydroxide, ammonia or ammonia water, or acid compounds, such as phosphoric acid or sulfuric acid, are expediently used. In order to control the development of foam, anti-foams, such as, for example, fatty acid polyglycol esters, may be used. In order to maintain the stability of plasmids, suitable substances having a selective action, such as, for example, antibiotics, may be added to the medium. In order to maintain aerobic conditions, oxygen or gas mixtures containing oxygen, such as, for example, air, are introduced into the culture. The temperature of the culture is normally from 20° C. to 45° C. and preferably from 25° C. to 40° C. The culture is continued until the maximum amount of the desired product has formed. That aim is normally achieved within a period of from 10 hours to 160 hours.

Methods of determining L-amino acids are known from the prior art. The analysis may be carried out, for example, as described in Spackman et al. (Analytical Chemistry, 30, (1958), 1190) by anion-exchange chromatography with subsequent ninhydrin derivatization, or it may be carried out by reversed phase HPLC, as described in Lindroth et al. (Analytical Chemistry (1979) 51: 1167–1174).

The following microorganisms were deposited at the Deutsche Sammlung fur Mikroorganismen and Zellkulturen (DSMZ, Braunschweig, Germany) in accordance with the Budapest Treaty:

Escherichia coli strain TOPIOF/pCR2.1luxRint as DSM 13619.

The process of the invention is used for the production of amino acids, in particular L-lysine, by fermentation.

The present invention is explained in greater detail below by means of Examples.

The isolation of plasmid DNA from *Escherichia coli* and all techniques for restriction, Klenow and alkaline phosphatase treatment were carried out according to Sambrook et al. (Molecular Cloning. A Laboratory Manual, 1989, Cold Spring Harbour Laboratory Press, Cold Spring Harbor, N.Y., USA). Methods for the transformation of *Escherichia coli* are also described in that handbook.

The composition of common nutrient media, such as LB or TY medium, will also be found in the handbook of Sambrook et al.

EXAMPLE 1

Preparation of a Genomic Cosmid Gene Library from *C. glutamicum* ATCC 13032

Chromosomal DNA from *C. glutamicum* ATCC 13032 was isolated as described in Tauch et al. (1995, Plasmid 33:168–179) and partially cleaved with the restriction enzyme Sau3AI (Amersham Pharmacia, Freiburg, Germany, product description Sau3AI, Code no. 27-0913-02). The DNA fragments were dephosphorylated with shrimp alkaline phosphatase (Roche Molecular Biochemicals, Mannheim, Germany, product description SAP, Code no. 1758250). The DNA of cosmid vector SuperCosl (Wahl et al. (1987), Proceedings of the National Academy of Sciences, USA 84:2160–2164), obtained from Stratagene (La Jolla, USA, product description SuperCosl Cosmid Vektor Kit, Code no. 251301), was cleaved with the restriction enzyme XbaI (Amersham Pharmacia, Freiburg, Germany, product description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, product description BamHI, Code no. 27-0868-04). The cosmid DNA so treated was mixed with the treated ATCC 13032 DNA, and the batch was treated with T4-DNA lipase (Amersham Pharmacia, Freiburg, Germany, product description T4-DNA lipase, Code no. 27-0870-04). The ligation mixture was then packed in phages with the aid of Gigapack II XL Packing Extract (Stratagene, La Jolla, USA, product description Gigapack II XL Packing Extract, Code no. 200217).

For infection of *E. coli* strain NM554 (Raleigh et al. 1988, Nucleic Acid Res. 16:1563–1575), the cells were taken up in 10 MM MgSO4 and mixed with an aliquot of the phage suspension. Infection and titration of the cosmid library were carried out as described in Sambrook et al. (1989, Molecular Cloning: A Laboratory Manual, Cold Spring Harbor), the cells being plated out on LB agar (Lennox, 1955, Virology, 1:190)+100 gg/ml ampicillin. After incubation overnight at 37° C., recombinant individual clones were selected.

EXAMPLE 2

Isolation and Sequencing of the luxR Gene

The cosmid DNA of an individual colony was isolated using the Qiaprep Spin Miniprep Kit (Product No. 27106, Qiagen, Hilden, Germany) according to the manufacturer's instructions, and partially cleaved with the restriction enzyme Sau3AI (Amersham Pharmacia, Freiburg, Germany, product description Sau3AI, Product No. 27-0913-02). The DNA fragments were dephosphorylated with shrimp alkaline phosphatase (Roche Molecular Biochemicals, Mannheim, Germany, product description SAP, Product No. 1758250). After separation by gel electrophoresis, cosmid fragments having a size in the range from 1500 to 2000 by were isolated using the QiaExII Gel Extraction Kit (Product No. 20021, Qiagen, Hilden, Germany).

The DNA of sequencing vector pZero-1, obtained from Invitrogen (Groningen, Netherlands, product description Zero Background Cloning Kit, Product No. K2500-01), was cleaved with the restriction enzyme BamHI (Amersham Pharmacia, Freiburg, Germany, product description BamHI, Product No. 27-0868-04). Ligation of the cosmid fragments into the sequencing vector pZero-1 was carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). The ligation mixture was then electroporated into *E. coli* strain DHSaMCR (Grant, 1990, Proceedings of the National Academy of Sciences, U.S.A., 87:4645–4649) (Tauch et al. 1994, FEMS Microbiol Letters, 123:343–347) and plated out on LB agar (Lennox, 1955, Virology, 1:190) with 50 gg/ml Zeocin.

Plasmid preparation of the recombinant clones was carried out using the Biorobot 9600 (Product No. 900200, Qiagen, Hilden, Germany). Sequencing was effected by the dideoxy chain termination method of Sanger et al. (1977, Proceedings of the National Academies of Sciences, U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. Separation by gel electrophoresis and analysis of the sequencing reaction was carried out in a "Rotiphorese NF Acrylamid/Bisacrylamid" gel (29:1) (Product No. A124.1, Roth, Karlsruhe, Germany) using the "ABI Prism 377" sequencing device from PE Applied Biosystems (Weiterstadt, Germany).

The resulting crude sequence data were then processed using the Staden program package (1986, Nucleic Acids Research, 14:217–231) version 97-0. The individual sequences of the pZero1 derivatives were assembled to a coherent contig. The computer-assisted coding region analysis was prepared using the program XNIP (Staden, 1986, Nucleic Acids Research, 14:217–231). Further analyses were carried out using the "BLAST search program" (Altschul et al., 1997, Nucleic Acids Research, 25:33893402) against the non-redundant data bank of the "National Center for Biotechnology Information" (NCBI, Bethesda, Md., USA).

The resulting nucleotide sequence is shown in SEQ ID No. 1. Analysis of the nucleotide sequence gave an open reading frame of 639 bp, which was designated the luxR gene. The luxR gene codes for a polypeptide of 212 amino acids.

EXAMPLE 3

Preparation of an Integration Vector for Integration Mutagenesis of the luxR Gene Chromosmal DNA was isolated from strain ATCC 13032 by the method of Eikmanns et al. (Microbiology 140: 1817–1828 (1994)). On the basis of the sequence of the luxR gene known from Example 2 for *C. glutamicum*, the following oligonucleotides were selected for the polymerase chain reaction:

```
luxRintA:
5'GGA ATC GAC GTC ATC TTG AT 3'    (SEQ ID NO:4)

luxRintB:
5'GCA ACC AGC TTG AGA ACT TC 3'    (SEQ ID NO:5)
```

The primers shown were synthesised by MWG Biotech (Ebersberg, Germany), and the PCR reaction was carried out according to the standard PCR method of Innis et al. (PCR protocols. A Guide to Methods and Applications, 1990, Academic Press) using Pwo polymerase from Boehringer. With the aid of the polymerase chain reaction, an internal fragment of the luxR gene having a size of 353 by was isolated and is shown in SEQ ID No. 3.

The amplified DNA fragment was ligated into vector pCR2.1TOPO (Mead et al. (1991), Bio/Technology 9:657–663) using the TOPO TA Cloning Kit from Invitrogen Corporation (Carlsbad, Calif., USA; Catalog Number K4500-01).

*E. coli* strain TOP10F was then transformed with the ligation batch (Hanahan, in: DNA cloning. A Practical Approach. Vol. 1, IRL-Press, Oxford, Washington D.C., USA, 1985). The selection of plasmid-carrying cells was carried out by plating out the transformation batch on LB agar (Sambrook et al., Molecular Cloning: A Laboratory Manual. 2nd ed., Cold Spring Harbor Laboratory Press, Cold Spring Harbor, N.Y., 1989) which had been supplemented with 25 mg/l kanamycin. Plasmid DNA was isolated from a transformant with the aid of the QIAprep Spin Miniprep Kit from Qiagen and was tested by restriction with the restriction enzyme EcoRI and subsequent agarose gel electrophoresis (0.8%). The plasmid was named pCR2.1luxRint.

EXAMPLE 4

Integration Mutagenesis of the luxR Gene in the Lysine Producer DSM 5715

Vector pCR2.1luxRint mentioned in Example 3 was electroporated in *C. glutamicum* DSM 5715 by the electroporation method of Tauch et al. (FEMS Microbiological Letters, 123:343–347 (1994)). Strain DSM 5715 is an AECresistant lysine producer. Vector pCR2.1luxRint is unable to replicate independently in DSM 5715 and is retained in the cell only if it has integrated into the chromosome of DSM 5715. The selection of clones with pCR2.1luxRint integrated into the chromosome was effected by plating out the electroporation batch on LB agar (Sambrook et al., Molecular Cloning: A Laboratory Manual. 2nd ed., Cold Spring Harbor Laboratory Press, Cold Spring Harbor, N.Y.) which had been supplemented with 15 mg/l kanamycin.

In order to demonstrate the integration, the luxRint fragment was labelled by the method "The DIG System Users Guide for Filter Hybridization" from Boehringer Mannheim GmbH (Mannheim, Germany, 1993) using the Dig hybridization kit from Boehringer. Chromosomal DNA of a potential integrant was isolated by the method of Eikmanns et al. (Microbiology 140: 1817–1828 (1994)) and cleaved with each of the restriction enzymes SalI, SacI and HindIII. The resulting fragments were separated by means of agarose gel electrophoresis and hybridized at 68° C. using the Dig hybridization kit from Boehringer. Plasmid pCR2.1luxRint mentioned in Example 3 had inserted into the chromosome of DSM 5715 within the chromosomal luxR gene. The strain was designated DSM 5715::pCR2.1luxRint.

EXAMPLE 5

Production of L-lysine

The *C. glutamicum* strain DSM 5715::pCR2.1luxRint obtained in Example 4 was cultivated in a nutrient medium suitable for the production of L-lysine, and the L-lysine content in the culture supernatant was determined.

To that end, the strain was first incubated for 24 hours at 33° C. on agar plate with the corresponding antibiotic (brain-heart agar with kanamycin (25 mg/l). Starting from that agar plate culture, a pre-culture was inoculated (10 ml of medium in 100 ml Erlenmeyer flasks). CgIII complete medium was used as the medium for the pre-culture.

|  | Cg III medium |
| --- | --- |
| NaCl | 2.5 g/l |
| Bacto-peptone | 10 g/l |
| Bacto-yeast extract | 10 g/l |
| Glucose (autoclaved separately) | 2% (w/v) |

The pH value was adjusted to pH 7.4

Kanamycin (25 mg/l) was added thereto. The pre-culture was incubated for 24 hours at 33° C. at 240 rpm on a shaker. A main culture was inoculated from that pre-culture, so that the initial OD (660 nm) of the main culture was 0.1 OD. MM medium was used for the main culture.

| | MM medium |
|---|---|
| CSL (corn steep liquor) | 5 g/l |
| MOPS | 20 g/l |
| Glucose (autoclaved separately) | 50 g/l |
| Salts: | |
| $(NH_4)_2SO_4$ [sic] | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H2O$ | 5.0 mg/l |
| Biotin (sterilised by filtration) | 0.3 mg/l |
| Thiamin * HCl (sterilised by filtration) | 0.2 mg/l |
| Leucine (sterilised by filtration) | 0.1 g/l |
| $CaCO_3$ | 25 g/l |

CSL, MOPS and the salt solution are adjusted to pH 7 with ammonia water and autoclaved. The sterile substrate and vitamin solutions are then added, as well as the dry autoclaved CaCO3.

Cultivation is carried out in a volume of 10 ml in a 100 ml Erlenmeyer flask with baffles. Kanamycin (25 mg/l) was added. Cultivation was carried out at 33° C. and 80% humidity.

After 72 hours, the OD was determined at a measuring wavelength of 660 nm using a Biomek 1000 (Beckmann Instruments GmbH, Munich). The amount of L-lysine that had formed was determined using an amino acid analyzer from Eppendorf-BioTronik (Hamburg, Germany) by ion-exchange chromatography and post-column derivatization with i ninhydrin detection.

The result of the test is shown in Table 1.

TABLE 1

| Strain | OD (660) | Lysine Hcl g/l |
|---|---|---|
| DSM 5715 | 7.5 | 13.01 |
| DSM 5715::pCR2.1luxRint | 8.8 | 15.41 |

What is claimed is:

1. A process for producing L-amino acids comprising culturing a coryneform bacterium in a medium suitable for producing L-amino acids, wherein said coryneform bacterium comprises a luxR gene the expression of which is attenuated by a disruotion of, a replacement or, a deletion of, or a codon substitution in, all or part of a nucleic acid sequence encoding a polypeptide having an amino acid sequence at least 95% identical to the amino acid sequence set forth in SEQ ID NO:2 and that regulates the biosynthesis of lysine and valine in a coryneform bacterium.

2. The process of claim 1, wherein said bacterial cell is selected from the group consisting of Coryneform glutamicum, Corynebacterium acetoglutamicum, Corynebacterium acetoacidophilum, Corynebacterium melassecola, Corynebacterium thermoaminogenes, and Brevibacterium flavum.

3. The process of claim 1, wherein said luxR gene prior to being attenuated comprises the polynucleotide sequence of SEQ ID NO:1.

4. The process of claim 1, wherein said L-amino acid is L-lysine.

5. The process of claim 1, wherein said L-amino acid is L-valine.

6. The process of claim 1, wherein said coryneform bacterium further comprises at least one gene whose expression is attenuated, wherein said gene is selected from the group consisting of pck, pgi, and poxB.

7. The process of claim 1, wherein said luxR gene prior to being attenuated comprises a polynucleotide sequence which encodes the amino acid sequence of SEQ ID NO:2.

8. The process of claim 1, wherein at least one of the dapA, eno, zwf, pyc, and lysE genes is overexpressed in said coryneform bacterium.

9. The process of claim 6, wherein the expression of at least one of the pck, pgi, and poxB genes is inactivated.

* * * * *

SEQUENCE LISTING

```
<160> NUMBER OF SEQ ID NOS: 5

<210> SEQ ID NO 1
<211> LENGTH: 1052
<212> TYPE: DNA
<213> ORGANISM: Corynebacterium glutamicum
<220> FEATURE:
<221> NAME/KEY: CDS
<222> LOCATION: (214)..(849)
<223> OTHER INFORMATION:

<400> SEQUENCE: 1
tgcagcattg ccggtggagc caccagaggg gtttgtcggg gcgccggttt tggcagattc      60
ggactcaagt gctacaggcg aggttgaact aagttctcca actgacgatg agtaaggcta     120
gactaaagta cgattcatct gctcatcgat actcttgaag gcgcattttc attcgaaacg     180
aagtgcgcca ttgggaagga cctagttcaa aca atg att cgc gtg ctg ctt gct     234
                                    Met Ile Arg Val Leu Leu Ala
                                     1               5 gat gac cac gaa atc gtg agg ctc gga ctc cga gct gtg ctg gaa agc     282
Asp Asp His Glu Ile Val Arg Leu Gly Leu Arg Ala Val Leu Glu Ser
        10                  15                  20 gcc gag gac att gaa gtg gtg ggc gaa gtc tcc acc gcc gaa ggt gcg     330
Ala Glu Asp Ile Glu Val Val Gly Glu Val Ser Thr Ala Glu Gly Ala
    25                  30                  35 gtg cag gca gcc caa gaa ggc gga atc gac gtc atc ttg atg gac ctc     378
Val Gln Ala Ala Gln Glu Gly Gly Ile Asp Val Ile Leu Met Asp Leu
40                  45                  50                  55 cga ttc ggc ccc ggc gtc caa gga acc cag gtt tcc aca ggc gca gac     426
Arg Phe Gly Pro Gly Val Gln Gly Thr Gln Val Ser Thr Gly Ala Asp
                60                  65                  70
```

```
gcc acc gca gcc atc aag cga aac atc gat aac ccg cca aaa gtc ctg       474
Ala Thr Ala Ala Ile Lys Arg Asn Ile Asp Asn Pro Pro Lys Val Leu
            75                  80                  85 gtc gtg acc aac tac gac acc gac aca gac atc ctc ggc gca atc gaa       522
Val Val Thr Asn Tyr Asp Thr Asp Thr Asp Ile Leu Gly Ala Ile Glu
            90                  95                  100 gcc ggc gca ctg ggc tac ctg ctc aaa gac gcc cca ccg agc gaa ctc       570
Ala Gly Ala Leu Gly Tyr Leu Leu Lys Asp Ala Pro Pro Ser Glu Leu
        105                 110                 115 ctg gca gca gta cga tcc gca gca gaa ggt gac tcc aca ctg tca ccc       618
Leu Ala Ala Val Arg Ser Ala Ala Glu Gly Asp Ser Thr Leu Ser Pro
120                 125                 130                 135 atg gtt gcg aac cgc ctg atg act cgc gtg cgc acc ccc aaa acc tca       666
Met Val Ala Asn Arg Leu Met Thr Arg Val Arg Thr Pro Lys Thr Ser
                140                 145                 150 ctc acc cca cgt gaa ctg gaa gtt ctc aag ctg gtt gcc ggt gga tcc       714
Leu Thr Pro Arg Glu Leu Glu Val Leu Lys Leu Val Ala Gly Gly Ser
                155                 160                 165 tcc aac cgc gac att ggc cgt atc ctc ttc ctc tca gaa gcc acg gtg       762
Ser Asn Arg Asp Ile Gly Arg Ile Leu Phe Leu Ser Glu Ala Thr Val
        170                 175                 180 aaa tcc cac ctc gtg cac atc tac gac aag ctc ggc gtg cgg tca cgt       810
Lys Ser His Leu Val His Ile Tyr Asp Lys Leu Gly Val Arg Ser Arg
185                 190                 195 acc tcc gct gtc gca gcc gca cgt gag cag ggg ctg ctg tagcggggt         859
Thr Ser Ala Val Ala Ala Ala Arg Glu Gln Gly Leu Leu
200                 205                 210 tgctgcaagg ctttaggtat ccgcgccggg gttggcctac gggagcatcc cgaggcttta    919
gcaggggcac gggctctggc ttgggctgag tcagggcgc ggccaatgct ttccgacgcg     979
tgtctccacg gctttattta gtttttcaag aagtttgacg aaggtgcgta gatcctcttc   1039
gggccagtct gaa                                                      1052

<210> SEQ ID NO 2
<211> LENGTH: 212
<212> TYPE: PRT
<213> ORGANISM: Corynebacterium glutamicum

<400> SEQUENCE: 2

Met Ile Arg Val Leu Leu Ala Asp Asp His Glu Ile Val Arg Leu Gly
1               5                   10                  15

Leu Arg Ala Val Leu Glu Ser Ala Glu Asp Ile Glu Val Val Gly Glu
            20                  25                  30

Val Ser Thr Ala Glu Gly Ala Val Gln Ala Ala Gln Glu Gly Gly Ile
        35                  40                  45

Asp Val Ile Leu Met Asp Leu Arg Phe Gly Pro Gly Val Gln Gly Thr
    50                  55                  60

Gln Val Ser Thr Gly Ala Asp Ala Thr Ala Ile Lys Arg Asn Ile
65                  70                  75                  80

Asp Asn Pro Pro Lys Val Leu Val Thr Asn Tyr Asp Thr Asp Thr
                85                  90                  95

Asp Ile Leu Gly Ala Ile Glu Ala Gly Ala Leu Gly Tyr Leu Leu Lys
            100                 105                 110

Asp Ala Pro Pro Ser Glu Leu Leu Ala Ala Val Arg Ser Ala Ala Glu
        115                 120                 125

Gly Asp Ser Thr Leu Ser Pro Met Val Ala Asn Arg Leu Met Thr Arg
    130                 135                 140
```

```
Val Arg Thr Pro Lys Thr Ser Leu Thr Pro Arg Glu Leu Glu Val Leu
145                 150                 155                 160

Lys Leu Val Ala Gly Gly Ser Ser Asn Arg Asp Ile Gly Arg Ile Leu
            165                 170                 175

Phe Leu Ser Glu Ala Thr Val Lys Ser His Leu Val His Ile Tyr Asp
            180                 185                 190

Lys Leu Gly Val Arg Ser Arg Thr Ser Ala Val Ala Ala Ala Arg Glu
            195                 200                 205

Gln Gly Leu Leu
    210

<210> SEQ ID NO 3
<211> LENGTH: 353
<212> TYPE: DNA
<213> ORGANISM: Corynebacterium glutamicum

<400> SEQUENCE: 3
ggaatcgacg tcatcttgat ggacctccga ttcggccccg gcgtccaagg aacccaggtt      60
tccacaggcg cagacgccac cgcagccatc aagcgaaaca tcgataaccc gccaaaagtc     120
ctggtcgtga ccaactacga caccgacaca gacatcctcg gcgcaatcga agccggcgca     180
ctgggctacc tgctcaaaga cgccccaccg agcgaactcc tggcagcagt acgatccgca     240
gcagaaggtg actccacact gtcacccatg gttgcgaacc gcctgatgac tcgcgtgcgc     300
acccccaaaa cctcactcac cccacgtgaa ctggaagttc tcaagctggt tgc            353

<210> SEQ ID NO 4
<211> LENGTH: 20
<212> TYPE: DNA
<213> ORGANISM: Corynebacterium glutamicum

<400> SEQUENCE: 4
ggaatcgacg tcatcttgat                                                  20

<210> SEQ ID NO 5
<211> LENGTH: 20
<212> TYPE: DNA
<213> ORGANISM: Corynebacterium glutamicum

<400> SEQUENCE: 5
gcaaccagct tgagaacttc                                                  20
```